United States Patent [19]

Richmond et al.

[11] Patent Number: 5,310,669

[45] Date of Patent: May 10, 1994

[54] FULLERENE COATED SURFACES AND USES THEREOF

[75] Inventors: Robert C. Richmond, Etna; Ursula J. Gibson, West Lebanon, both of N.H.

[73] Assignee: The Trustees of Dartmouth College, Hanover, N.H.

[21] Appl. No.: 901,911

[22] Filed: Jun. 22, 1992

[51] Int. Cl.$^5$ .......................... C12M 3/00; C12N 5/00; C12N 11/00; C12N 11/02

[52] U.S. Cl. .................................. 435/177; 435/174; 435/240.2; 435/240.23; 435/240.243; 435/284

[58] Field of Search ............... 435/174, 177, 180, 181, 435/240.1, 240.2, 240.23, 240.241, 240.243, 240.242, 284, 285

[56] References Cited

U.S. PATENT DOCUMENTS

| | | | |
|---|---|---|---|
| 4,363,634 | 12/1982 | Schall, Jr. | 435/181 |
| 4,438,196 | 3/1984 | Lantero, Jr. | 435/181 |
| 5,108,923 | 4/1992 | Benedict et al. | 435/240.23 |

OTHER PUBLICATIONS

Abstracts of Papers for the Fortieth Annual Meeting of the Radiation Research Society, Salt Lake City, Utah, Mar. 14-18, 1992 "Uptake of Water-Soluble Metalloporphyrins by Murine Adenocarcinoma (MTG-B) Cells and Tumors", J. A. O'Hara, R. C. Richmond (P-27-3).

"Solid $C_{60}$: A New Form of Carbon", W. Kratschmer et al., Nature,, vol. 347, pp. 354-358 (27 Sep. 1990).

"The Higher Fullerenes: Isolation and Characterization of $C_{76}$, $C_{84}$, $C_{90}$, and $C_{70}O$, and Oxide of $D_{5h}$-$C_{70}$", Francois Diederich et al., Science, vol. 252, pp. 548-551 (26 Apr. 1991).

James W. Arbogast et al., J. Phys. Chem., 1991, 95, 12-19.

Johan Moan, Journal of Photochemistry and Photobiology, B: Biology, 6 (1990) 343-347.

Kunihiko Suwa et al., Biochemical and Biophysical Research Communications, vol. 75, No. 3, 1977.

"The Chemical Nature of Buckminsterfullerene ($C_{60}$) and the Characterization of a Platinum Derivative", Paul J. Fagan et al., Science, 252, 1160-1161 (May 1991).

"Electronic Structure, Conductivity, and Superconductivity of Alkali Metal Doped $C_{60}$", R. C. Haddon, Acc. Chem. Res. 1992, 25, 127-133.

"Atomic Force Microscope Studies of Fullerene Films: Highly Stable $C_{60}$ fcc (311) Free Surfaces", Eric J. Snyder et al., Science, 253, 171-173 (Jul. 1991).

"Effect of Activated Charcoal on the Disposition of Sulphadoxine", A. Akintonwa and O. Obodozie, Arch. int. Pharmacodyn, 309, 185-192 (1991).

"Clinical Pharmacokinetics of Oral Activated Charcoal in Acute Intoxications", Pertti J. Neuvonen, Clinical Pharmacokinetics 7:465-489 (1982).

"Interaction of $O_2$ with $C_{60}$: photon-induced oxidation", G. H. Kroll et al., Chemical Physics Letters, vol. 181, No. 2.3, 21 Jun. 1991.

"Characterization of the Soluble All-Carbon Molecules $C_{60}$ and $C_{70}$", Henry Ajie et al., J. Phys. Chem, 1990, 94, 8630-8633.

"Efficient Production of $C_{60}$ (Buckminsterfullerene), $C_{60}H_{36}$, and the Solvated Buckide", R. E. Haufler et al., J. Phys. Chem. 1990, 94, 8634-8636.

"Mechanism of Mammalian Cell Lysis Mediated by Peptide Defensins", Alan Lichtenstein. The Journal of Clinical Investigation, Inc., vol. 88, Jul. 1991, 93-100.

"Conducting $C_{60}$, $C_{70}$ films produced", Science/Technology, p. 59, Apr. 8, 1991 C&EN.

"Radical Reactions of $C_{60}$", P. J. Krusic et al., Science, vol. 254, 1183-1185, 22 Nov. 1991.

"Rat Enterocyte Injury by Oxygen-Dependent Processes", Susan S. Baker and Cara L. Campbell, Gastroenterology 1991; 101:716-720.

Primary Examiner—Robert J. Warden
Assistant Examiner—L. M. Crawford
Attorney, Agent, or Firm—Lahive & Cockfield

[57] ABSTRACT

Substrates having a surface coated with fullerene and a substance attached thereto are disclosed. Cell culture substrates having a fullerene-coated surface are useful in methods of growing cells on the fullerene-coated surface. Methods of preparing cell culture substrates for cell attachment and growth by coating a surface with fullerene are provided. Cells can be grown on a fullerene-coated surface in the presence of a substance such as a cytokine, growth hormone or a drug, to evaluate the interaction between the substance and the cells. Methods for increasing cell membrane premability and for introducing a substance, such as a DNA or RNA vector, into a cell are also provided.

16 Claims, 9 Drawing Sheets

FULLERENE COATED SURFACES AND USES THEREOF

BACKGROUND OF THE INVENTION

As a class, the recently discovered third allotropic form of carbon is termed fullerenes, and the prototypical form of this class is a spherical hollow molecule containing 60 carbon atoms, i.e., $C_{60}$, that is termed buckminsterfullerene (Kratschmer, W., et al., *Nature* 347:354–357 (1990); Ajie, H. et al., *J. Phys. Chem.*, 94:8630–8633 (1990); and Diederich, F., et al., *Science.* 252:548–551 (1991)). The fullerene family includes asymmetrical forms, such as $C_{70}$, as well as cylindrical fibers nicknamed buckytubes. In $C_{60}$, hexagons and pentagons of carbon link together in a coordinated fashion to form a hollow, geodesic dome with bonding strains equally distributed among 60 carbon atoms. Some of the electrons are delocalized over the entire molecule, similar to benzene. However, benzene is flat and many of its derivatives tend to stack in flat sheets. Spherical $C_{60}$ adds a new dimension to the chemistry of aromatic compounds.

$C_{60}$ has been shown to be one of the most chemically versatile molecules known. Chemists have produced fullerene derivatives by adding carbons to the $C_{60}$ sphere while maintaining (in some instances) the aromatic electron structure. $C_{60}$ has been reported to readily accept free radicals and may be useful in polymerization processes. Other potential applications include commercial basics such as catalysis as well as superconductivity and ferromagnetism. $C_{60}$ easily accepts electrons. Solid fullerene can also be doped with an alkali metal such as potassium, and these compounds are called fullerides. Although pure $C_{60}$ is an insulator, some fullerides are semiconductors or superconductors; for example, $K_3C_{60}$ is a superconductor.

$C_{60}$, a naturally hollow molecule, has been proposed as a host for nuclides. In addition, unmodified fullerenes are insoluble in water, suggesting that they may react very little with biological tissue. In the presence of light and oxygen, the $C_{60}$ molecule can pass its excitation energy onto nearby oxygen molecules, creating a short-lived, reactive form of oxygen called singlet oxygen.

SUMMARY OF THE INVENTION

This invention pertains to substrates having a surface coated with fullerene and to the use of such substrates for immobilization and/or manipulation of substances on the surface. The fullerene-coated surface can be used to immobilize a wide variety of biological materials such as cells, macromolecules and drugs. In one embodiment, a surface of a substrate is coated with fullerene and used for attachment and growth of cells. Cell culture substrates having a fullerene-coated surface are useful in methods of growing cells on the fullerene-coated surface. Methods of preparing cell culture substrates for cell attachment and growth by coating a surface with fullerene are disclosed. Cell culture substrates having a fullerene-coated surface can be conditioned for cell attachment and growth by growing a first population of cells on the fullerene-coated surface and exposing the cells to a solvent, such as sulfolane combined with 7% perchloric acid and 3% water, designated herein as SPCA, to remove the cells from the fullerene-coated surface. Subsequently, cell material and solvent is removed from the surface to produce a regenerated fullerene-coated surface. A second population of cells can then be grown on the regenerated fullerene-coated surface and maintained under conditions appropriate for cell growth. Alternatively, the fullerene-coated surface can be conditioned for cell attachment and growth by coating the fullerene-coated surface with a cell attachment factor.

The invention also provides methods of growing cells on fullerene-coated surfaces in the presence of a substance such as a cytokine, antigen, hormone or drug, and to evaluate the interaction between the substance and the cell. Methods for damaging the plasma membrane, for increasing cell membrane permeability, and for introducing substances into a cell are also provided. Such methods comprise first attaching cells to a cell culture substrate having a fullerene-coated surface and maintaining the cells under conditions appropriate for cell growth. The cells are then illuminated with light in the presence of oxygen to damage the cell membrane and thereby increase cell membrane permeability. Subsequently, or prior to illumination, the cells are contacted with a substance to be introduced into the cells. The increased cell membrane permeability allows the substance to be introduced into the cell. The method is useful for transfecting a cell with, for example, a vector comprising DNA or RNA.

DETAILED DESCRIPTION OF THE INVENTION

Figure 1:
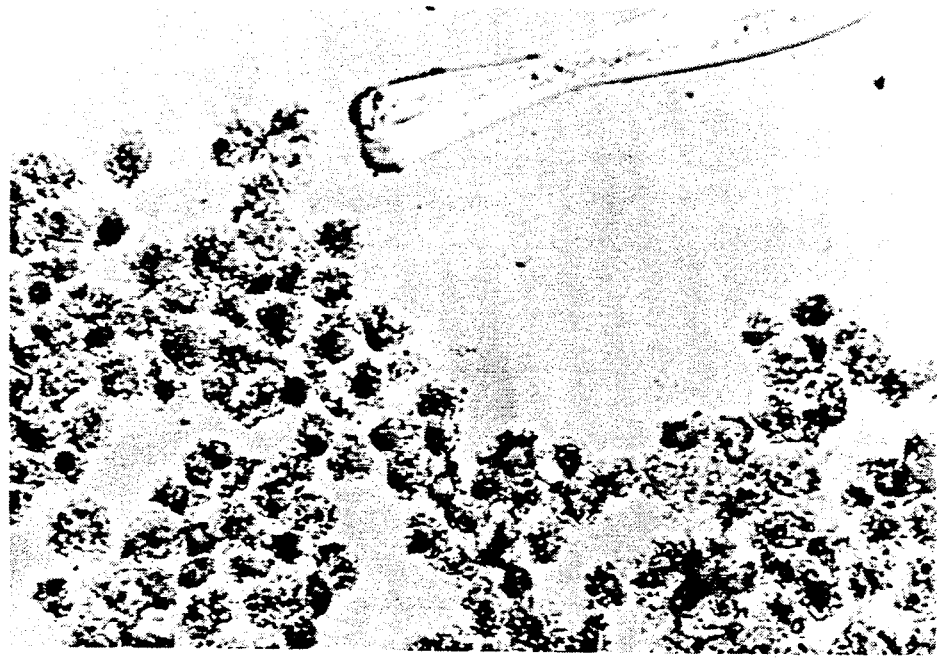
FIG. 1 shows remaining patches of CHO-AA8 cells grown to confluency on a glass slip (designated Slip #3) having a vapor deposited fullerene surface and illuminated in the presence of oxygen followed by trypsinization and trypan blue staining.

Fullerenes are commonly derived by contact-arc vaporization of a graphite rod, which results in the formation of raw soot. The raw soot produced by this process primarily comprises a mixture of two fullerenes, $C_{60}$ and $C_{70}$ in a ratio of about 10 to 1 respectively, accounting for about 5 to 10% of the total soot. Other methods of deriving fullerene-containing soot, primarily from sooting flames, also exist. Fullerenes such as $C_{60}$, $C_{70}$, $C_{76}$, $C_{78}$, $C_{84}$, etc., can be deposited on a substrate alone following purification, or as a mixture with one or more fullerenes.

Fullerenes can be recovered from raw soot by extraction with organic solvents, such as benzene or toluene, followed by precipitative or evaporative deposition of the fullerenes on a surface of a substrate and solvent removal. Alternatively, fullerenes can be recovered by sublimation under vacuum with fullerene vapor being condensed as a film upon a relatively cool substrate surface. Fullerenes can also be coated on the surface of a substrate by ion-sputtering of purified fullerene or raw unprocessed fullerene-containing soot.

Fullerenes coated to a surface of a substrate are useful for immobilizing and/or manipulating substances on the surface. The fullerene-coated surface can be used to immobilize biological materials including cells, macromolecules, drugs, aromatic molecules, and aliphatic substances.

In one embodiment, fullerene coated surfaces are used as a substrate for cell growth. Cells are cultured in an appropriate media on a fullerene-coated surface of a cell culture substrate to facilitate cell attachment and growth. A surface of a cell culture substrate such as a ceramic, a polymer or a carbon matrix can be coated with fullerenes and used in methods of cell culture. Preferred ceramic cell culture substrates comprise glass or quartz. Polymer substrates useful for cell culture include polystyrene, polypropylene, polyhydroxyethyl methylacrylate, polyethylene terephthalate, polytetrafluoroethylene and nylon. A preferred polymer for forming a cell culture substrate is polystyrene. Useful cell culture substrates include devices such as cell culture flasks, cell culture dishes, cell culture microcarriers, cell culture macrocarriers, cell culture films and cell culture fibers.

Cell culture substrates having a fullerene-coated surface are useful in methods of growing cells. Cells are cultured on a cell culture substrate in an appropriate media (e.g., Dulbecco's Modified Eagle Media, CMRL Media, Minimum Essential Media or RPMI Media 1640 for mammalian cell lines) which may contain factors necessary for cell proliferation and viability, including animal serum (e.g., fetal bovine serum), hormones, protein growth factors, and antibiotics (e.g., penicillin, streptomycin). Additional factors, such as extracellular matrix components (e.g., collagen, fibronectin, and polylysine) or attachment peptides (e.g., RGD; Arg-Gly-Asp) can be coated on the cell culture substrate to enhance cell adhesion and growth. The cells are maintained under conditions necessary to support cell growth, for example an appropriate temperature (e.g., 37° C.) and atmosphere (e.g., air plus 5% $CO_2$).

Illumination of a fullerene in solution with absorbing light in the presence of molecular oxygen generates highly reactive singlet oxygen ($^1O_2$) by a semi-catalytic process without concurrent damage to the fullerene (Arbogast, J. W., et al., *J. Phys. Chem.* 95:11–12 (1991)). Substances, such as cells or macromolecules can therefore be attached to a fullerene-coated surface and illuminated with light in the presence of oxygen to induce $^1O_2$ damage. When cells are attached to a fullerene-coated surface, the reactivity of $^1O_2$ is such that it is unlikely to diffuse beyond the attached cell membrane (Moan, J., *J. Photochem. Photobiol. B: Biology* 6:343–344 (1990); Suwa, K., et al., *Biochem Biophys. Res. Comm.* 75:785–792 (1977)). Thus, the predominate oxidative reactions are likely to be peroxidations and cycloadditions of $^1O_2$ at carbon-to-carbon double bonds, resulting in increased cell membrane permeability. The length of illumination, intensity and wavelength of the light can be selected to quantitatively control the membrane induced damage. This technique is useful to study cell membrane composition e.g., cholesterol content, low- vs high-density lipoprotein interactions and the effect of oxidative damage on the cell membrane.

In addition, selective increases in cell membrane permeability allow the introduction of substances (e.g., a vector) into the cell. Cells attached to a fullerene-coated surface can be cultured with a substance to be introduced into the cell prior to, simultaneously with, or following illumination with light in the presence of oxygen. For example, membrane porosity can be manipulated to accommodate the entry of vectors, transfecting DNA, antibodies and other proteins, DNA pool intermediates, a drug, etc. As described in detail in the examples, Chinese Hamster Ovary (CHO) cells illuminated with light in the presence of oxygen were observed to take up trypan blue, an event indicating an increased permeability of the cell membrane (Lichtenstein, A., *J. Clin. Invest* 88:93–100 (1991); Baker, S. S., et al., *Gastroenterology* 101:716–720 (1991)). In addition, the cells illuminated in the presence of oxygen were shown to resist detachment by trypsinization or contraction by air drying, indicating treatment-induced bonding of cell constituents to the fullerene surface.

Singlet oxygen-induced damage to cell membranes can also be used to study the interaction and effects on cell growth and viability of various substances such as cytokines (e.g., interleukin-2), lectins (e.g., phytohemoglutinin), hormones, growth factors, oncogene products, monoclonal antibodies, ion-channel complexes, antigen receptors, DNA, RNA, polyethylene glycol, glycogen, drugs, aromatic molecules, steroids, phospholipids, long chain aliphatic substances and cell attachment factors. Membrane-related drug interactions can be probed, e.g., interactions with the antitumor drug adriamycin or with a variety of anesthetic agents. These substances can be co-cultured with cells on a fullerene-coated surface to evaluate the interaction between the substance and the cell. In addition, the cells can be cultured with the substance and illuminated in the presence of oxygen to determine the effect on the cell upon introduction of the substance into the cell or upon alteration of the cell membrane during illumination.

The fullerene structure is overall electrophilic, thus accounting for its tendency to react with electron rich reagents and free radicals (Haufler, R. E., et al., *J. Phys. Chem.*, 94:8634–8636 (1990); Fagan, P. J., et al., *Science* 252:1160–1161; Krusic, P. J., et al., *Science* 254:1183–1185 (1991)). This free radical reactivity may allow for controlled derivitizations of the fullerene surface for the purpose of directing specific cell membrane interactions. Derivatized fullerene surfaces would be useful for directing specific cell attachment and growth, as well as manipulating membrane damage by singlet oxygen.

An important feature of fullerenes is their ability to act as a form of "activated carbon". The fullerene electronic structure is a system of overlapping pi-orbitals, such that a multitude of bonding electrons are cooperatively presented around the surface of the molecule (*Chemical and Engineering News*. Apr. 8, 1991, page 59). This extensive system of overlapping pi-orbitals produces resonance hybrids with similarity to graphite, such that the longer the fullerene structure, the greater this similarity (Haddon, R. C., *Acc. Chem. Res.*, 25:127-133 (1992)). As a form of activated carbon, fullerenes exhibit substantial van der Waals forces for weak interactions. These weak interactions account for the well known adsorptive capacity of activated carbon (Hassler, J. W., *Active Carbon: The Modern purifier*, Githens-Sohl Corp, New York, 1941; Snyder, L. R., *Principles of Adsorption Chromatography*, Marcel Dekker, Inc., New york, 1968). The adsorptive nature of the fullerene surface may lend itself to additional modifications for the purpose of directing specific cell membrane interactions. For example, specific molecules that possess chemical properties that selectively bind to membranes of particular cell types or to particular components of cell membranes generally, e.g., lectins or antibodies can be adsorbed to the fullerene surface. The fullerene surface can be chemically modified to present specifically reactive groups to the cell membrane, e.g., oxidants or reductants. Attachment of different molecules to a fullerene surface could be manipulated to result in a surface which favors attachment of specific molecular or cell types, such as epithelial cells, fibroblasts, primary explants, or T-cell subpopulations by use of, for example, T-cell antigen receptors or antibody bound to the fullerene-coated surface.

The adsorptive nature of fullerenes can be exploited in methods of enhancing cell attachment to a fullerene-coated surface. In one embodiment, a fullerene-coated surface is conditioned for cell attachment and growth by growing a first population of cells on the fullerene-coated surface and exposing the cells to a solvent, e.g., SPCA, to remove the cells from the fullerene-coated surface. Subsequently, cell material and solvent is removed from the surface to produce a regenerated fullerene-coated surface. A second population of cells is grown on the regenerated fullerene-coated surface by maintaining the cells under conditions appropriate for cell growth. Suitable solvents include acidified sulfolane (e.g., acidified with perchloric acid (SPCA) or with trifluoromethane sulfonic acid), sulfolane alone, or other saturated or unsaturated ring system solvents having polar hydrophilic groups, as well as digestive enzyme solutions. For example, it was apparent by microscopic observation that CHO cells grown on surfaces coated with fullerene did not grow as rapidly or were as tightly attached (qualitatively judged by degree of rounding of cells attached to the surface) as cells attached to fullerene coated surfaces that were regenerated with SPCA for reuse. The superior cell attachment observed for these regenerated fullerene surfaces on either glass or plastic is likely due to absorption of cell-contained hydrophilic and/or receptor-like moieties to the carbon surface. Moreover, the solfolane of SPCA may have an affinity for activated carbon which explains the slightly enhanced cell attachment and growth observed for cells on SPCA-only treated fullerene surfaces given the hydrophilic non-bonding sulfoxide portion of the sulfolane molecule. SPCA is highly acidic, and sulfolane alone, or other saturated or unsaturated ring system solvents having polar hydrophilic groups, may be effective in conditioning the fullerene surface for subsequent cell attachment and growth. Thus, digestion or dissolution of a specific cell type or conditioning by specific adsorbing molecules on a fullerene surface may result in a modified fullerene surface that is selective for attachment and growth of a specific cell type from a mixed population of cells or that results in an improved surface for cell attachment and growth.

In another embodiment, a fullerene-coated surface is conditioned for cell attachment and growth by coating the fullerene-coated surface with an attachment factor prior to growing cells on the fullerene-coated surface. For example, CHO cells were found to have improved cell attachment on a fullerene-coated surface which had been treated with poly-L-lysine. The enhanced cell attachment is likely due to adsorption of this polymer to the active carbon surface. Other attachment factors, such as fibronectin and collagen can also be used.

The following non-limiting examples demonstrate fullerene retrieval from raw soot by vapor deposition of a fullerene film on either glass or plastic cell culture substrates, or by evaporative deposition on glass of $C_{60}$ dissolved in benzene. CHO cells were found to attach and grow on these fullerene-coated surfaces. In addition, illumination of the fullerene surface with light in the presence of molecular oxygen induced damage to the plasma membrane of the cells as indicated by the uptake of trypan blue and by visual observations of increased cell sticking to the supporting surface and by decreased symmetry of cell morphology.

EXAMPLE 1: SURFACE SUBSTRATES AND FULLERENE SURFACE PREPARATION

Purified $C_{60}$ was obtained as a gift from Dr. Christopher S. Foote, University of California at Los Angeles. Drops of magenta colored 1 mM solution of $C_{60}$ in benzene were spread on a 22×22 mm glass slip and evaporated leaving a yellowish gold microcrystalline residue that only partially covered the surface of the slip. Drops of a 1 mM solution of $C_{60}$ in benzene were also spread on the polystyrene surface of a petri dish and allowed to air dry, leaving a uniform magenta color at the plastic surface. Two-tenths of a ml of a 500 $\mu$m $C_{60}$ benzene solution covered a glass slip edge-to-edge, and was allowed to evaporate at ambient conditions leaving a yellowish film of $C_{60}$ interspersed with thicker plates of yellowish gold $C_{60}$ crystals.

Raw unprocessed fullerene-containing soot from carbon-arc vaporization of graphite rods was purchased from Materials and Electrochemical Research Corp. (Tucson, Ariz.). Approximately 0.1 to 0.2 g of this soot was moistened with methanol and loaded into a 0.375×1.00×0.375 inch molybdenum boat with a lid containing a small hole. The boat was suspended between two copper bars in a diffusion-pumped chamber. The substrates of glass or plastic to be coated were suspended above the boat by adhesive or by a through-drilled plate that exposed the majority of the substrate surface. Pressure was reduced to ca. $5 \times 10^{-5}$ Torr, at which point an AC current was driven through the boat, electrothermally heating it above the sublimation temperature of the fullerene contained in the raw soot. The rate and thickness of vapor deposition on the substrate were monitored using an oscillating quartz crystal. Conductive heating of raw soot in a vacuum chamber placed in a 550° C. sand bath also led to sublimation and deposition of fullerene surface on glass slide segments, glass slips, and polystyrene substrates suspended above the soot.

Glass slips used as substrate were no. 2 thickness from Corning; glass slides were 1 mm thick from Fisher. In one case, 2 slips and one slide were not thoroughly cleaned, i.e., had a barely discernible residue that appears to be resident on new slides and cover slips, prior to exposure to fullerene vapor; after fullerene exposure the slide was sectioned to pieces approximately the size of the slips. The latter two slips and slide had ca. 3 mm margins on two sides where fullerene deposition was not allowed, so as to afford the ability to distinguish differences in cell response on the same support surface. In a second case, 17 glass slide segments the size of slips were extensively cleaned by a chloroform rinse and polish, followed by ultrasonic cleaning in methanol prior to fullerene exposure. Several of these segments had masked margins to preclude fullerene deposition. In a third case, plastic dishes were taken as received from the manufacturer and subjected to fullerene vapor deposition; one dish type was unmodified polystyrene (Falcon bacteriological petri dish, no. 4-1008-3) and a second dish type was polystyrene made hydrophilic by proprietary superficial treatment with negatively charged groups, e.g., carboxyls and carbonates (information from Technical Service, Becton Dickinson Labware, Falcon Division) (Falcon tissue culture dish, no 4-3001-3). One of the polystyrene dishes had a 4 mm mask extending across its center where fullerene deposition was prevented.

One petri dish and one tissue culture polystyrene dish prepared with fullerene surfaces were treated with poly-L-lysine hydrobromide (PL) (Sigma P-2636, Type VII-B; approximate MW 60,000). A 100x stock solution was prepared by dissolving 34 mg of PL in 3.4 ml borate buffer (5.7 g sodium borate in 100 ml distilled water, adjusted to pH 8.4 with HCl), filter sterilized and aliquots frozen until use. Dilution of 1:100 was then made in sterile borate buffer. The surface of the fullerene-prepared dishes were covered with $1 \times PL$ solution, held 2 hours at 33° C., and rinsed exhaustively with PBS prior to seeding cells as described below.

The fullerene surface of one glass slip was directly scanned in a Perkin-Elmer Lambda 3A UV/VIS spectrophotometer, and then dissolved in benzene and this solution again scanned in the spectrophotometer. The integrity of the fullerene surface was qualitatively ascertained by visual and microscopic examination. Durability of the surface was ascertained as the continued integrity following autoclaving (glass substrate), exposure to and agitation with aqueous solutions as well as a solution of sulfolane containing 10% reagent grade perchloric acid (SPCA), and repetitive culturing of cells on the same fullerene surface following regeneration by exposure to SPCA. Vapor deposition of fullerene onto polystyrene or uncleaned glass resulted in a tightly attached film. Vapor deposition onto the freshly ultrasonically cleaned glass slide segments, however, provided a film that initially cracked upon subsequent autoclaving and was washed off from some segments by a water rinse; however, after a 3 month storage period under dark ambient conditions the remaining autoclaved segments were found to have their fullerene film tightly bonded to the glass substrate and thus resisted removal by vigorous rinsing or incubation with cells. It is thought that slow complexation with glass, or with charge groups in contaminants associated with the glass substrate, affords this bonding of fullerene films onto the ultrasonically cleaned glass surface.

EXAMPLE 2: CELL CULTURE AND ILLUMINATION OF CELLS ON FULLERENE COATED SURFACES

A Chinese Hamster Ovary (CHO) cell line designated AA8 was provided by Dr. Larry Thompson (Lawrence Livermore National Laboratory) (Hoy, C. A., et al., *Mutation Res.* 130:321–332 (1984)). About $3 \times 10^5$ cells were seeded into the prepared 35 mm dishes or dishes containing the prepared slips or slide segments and grown in alpha-MEM containing 10% fetal bovine serum, penicillin and streptomycin antibiotics and 40 nmol/liter 17-beta-estradiol (compete media) using an incubator at 37° C. equilibrated with air plus 5% $CO_2$. Slips, slide segments, and plastic dishes with fullerene surfaces regenereated for reuse by removing cells with treatment of SPCA contact for 2 hours at 33° C., followed by extensive washing with phosphate buffered saline, pH 7.0 (PBS), drying and autoclaving (glass only), and reseeding with CHO cells in complete media for regrowth.

Slips were placed in 32 mm glass dishes over a small stir bar, and were overlayed with complete media. This dish was placed on the bottom of a can-type vacuum chamber with a quartz window on top, and the media was stirred. For variable oxic control, two cycles of pumping the chambers to 52 mm Hg followed by backfilling with either 19% or 95% $O_2$ (plus 5% $C0_2$ balance $N_2$) were completed at room temperature in 1 minute, after which chambers were closed and samples held for an additional 10 minutes. For hypoxic equilibration, the chamber with cell sample was subjected to five cycles of pumping and back-filling with $N_2$ plus 5% $CO_2$ over the course of 20 minutes, followed by holding for an additional 10 minutes. After atmospheric manipulation, chambers were two-thirds immersed in a temperature-controlled water bath and held 7 minutes for equilibration at 35° C. Cells were then illuminated for 10 or 30 minutes through the window of the chamber using a Kodak Ektagraphic IIIB slide projector operating a 300 Watt incandescent lamp with output as previously described (Richmond, R. C., J. O'Hara, *Photochem. Photobiol.*, in press (1992)) such that irradiance to the cells was 98 $mW/cm^2$. Temperature rise during illumination plateaued after 10 minutes at 35° C., as separately monitored by a thermocouple placed in the sample media.

Following illumination, cells grown to confluency on initially deposited fullerene on glass slips were trypsinized from the fullerene surface using standard $1 \times$ porcine trypsin (ca. 1500 BAEE units/ml PBS, 30 minutes at 33° C.) and triturated to single cells. These cells were counted for trypan blue exclusion in a PBS solution of 0.08% trypan blue. One hundred cells (based on the trypan blue exclusion count) were plated in complete media and grown for 7 days at 37° C., after which time colonies were stained with methylene blue and counted. Cells resisting removal from the fullerene surface by $1 \times$ trypsin were found to take up trypan blue, and also to be removed by incubation with an additional exposure to $50 \times$ trypsin plus 0.02% disodium ethylenediaminetetraacetate (EDTA) for about 60 minutes at 33° C.

Alternatively, cells grown on an SPCA-regenerated fullerene surface on glass slips or slide segments were exposed directly after illumination to 0.08% trypan blue in PBS for 20 minutes at 33° C. followed in order by: 5 rinses in PBS; a 2 hour exposure to phosphate buffered 3.3% formaldehyde; a rinse in water; air drying; and microscopic assessment. In a third case, cells were similarly exposed to trypan blue and PBS rinsing after illumination, but were then treated with SPCA for 2 hours at 33° C., after which the fullerene surface was triturated and the SPCA solution of photometrically analyzed for trypan blue concentration at 568 nm using an extinction coefficient of $7.7 \times 10^4$ liter/mol.cm determined from trypan blue dissolved in SPCA alone.

EXAMPLE 3: ASSESSMENT OF CELL MEMBRANE PERMEABILITY FOLLOWING ILLUMINATION OF CELLS ON SURFACES PREPARED WITH PURIFIED FULLERENE

CHO cells were grown over the dispersed residue of yellowish gold microcrystalline $C_{60}$ left on the glass slip by evaporating drops of a 1 mM $C_{60}$ benzene solution, and were then illuminated under 95% $O_2$ plus 5% $CO_2$ for 30 minutes (147 J/cm$^2$). A small amount of foaming and cell clumping was noted when cells were then trypsinized, suggesting some membrane damage during illumination. Similar observations of minor membrane damage were made for CHO cells grown on a polystyrene surface exposed to a 1 mM solution of $C_{60}$ in benzene, treated with poly-L-lysine, and illuminated as described above. Although the surface of this plastic appeared dry after exposure to the $C_{60}$ solution, the magenta color of the solution was preserved, suggesting that a $C_{60}$ solution was maintained within the polymeric skein of the plastic. The continuous film of $C_{60}$ interspersed with crystalline plates resulting from evaporating 0.20 ml of 500 μM $C_{60}$ in benzene also supported confluent CHO cell growth, and 5 minutes of illumination in air led to cell damage as determined by increased cell sticking to the supporting surface and by decreased symmetry of cell morphology assumed to reflect damage to plasma membrane.

EXAMPLE 4: ASSESSMENT OF CELL MEMBRANE PERMEABILITY FOLLOWING ILLUMINATION OF CELLS ON A GLASS SUBSTRATE PREPARED BY FULLERNE VAPOR DEPOSITION

Two uncleaned glass slips (Slip #2 and Slip #3) were prepared with an approximate 500 nm thickness of fullerene by electrothermal vapor deposition from raw unprocessed carbon-arc soot, such that 3 mm glass-only margins were maintained on two edges of the slide. These slips were then autoclaved. The golden bronze fullerene surface was microscopically determined to be smooth and unflawed both before and after autoclaving. About 10$^6$ CHO-AA8 cells were seeded and grown to confluency, and this was noted to take 3 days on these fullerene-coated slips rather than the two days on the unprocessed glass slip (Slip #1).

Cells on Slip #1 were not further treated, whereas cells on Slips #2 and #3 were brought to 95% $O_2$ plus 5% $CO_2$ in complete media and illuminated at 37° C. for 10 minutes (59 J/cm$^2$) and 30 minutes (177 J/cm$^2$), respectively. Cells were then trypsinized from all slips in standard fashion. Slip #1 afforded an excellent single cell suspension with minimal trituration, yielding a total of $5.1 \times 10^6$ cells. Slips #2 and #3 afforded a clot of cells that lifted off the slip as a sticky mass that then provided only a partial yield of single cells (61% and 41% of the control number, respectively) in suspension after extensive trituration.

Trypan blue exclusion was determined, and 100 cells were plated in triplicate based on the trypan blue exclusion counts, and colonies were then scored. Results are shown in Table I.

TABLE I

| Slip # | % Trypan Blue Uptake | % Plating Efficiency (SD) | Surviving Fraction (SD) |
|---|---|---|---|
| 1 | 3 | 87 (10) | 1.00 (0.15) |
| 2 | 7 | 56 (7) | 0.64 (0.08) |
| 3 | 8 | 54 (6) | 0.62 (0.07) |

It is clear that the fraction of single cells recovered from the sticky mass of illuminated trypsinized cells were only slightly adversely affected in regards to membrane permeability (judged as trypan blue uptake) and inability to form colonies relative to control cells. Also clear is the fact that membrane damage did result from illumination of cells on fullerene surfaces due to the stickiness observed after trypsinization and the incomplete recovery of cells following extensive trituration.

Slips #2 and #3 were observed to retain patches of cells on the fullerene surfaces after 1×trypsin treatment. These 1×trypsin resistant cells were dissociated from Slip #2 by an additional 60 minutes incubation at 37° C. with 50×trypsin plus 0.02% EDTA. These resistant cells on Slip #3 were also found to take up trypan blue when covered with a 0.08% solution, as shown in FIG. 1 (magnification 480X) where the fullerene surface was scratched next to the photographed patch of cells in order to show the appearance and integrity of these vapor deposited fullerene surfaces.

Figure 2:
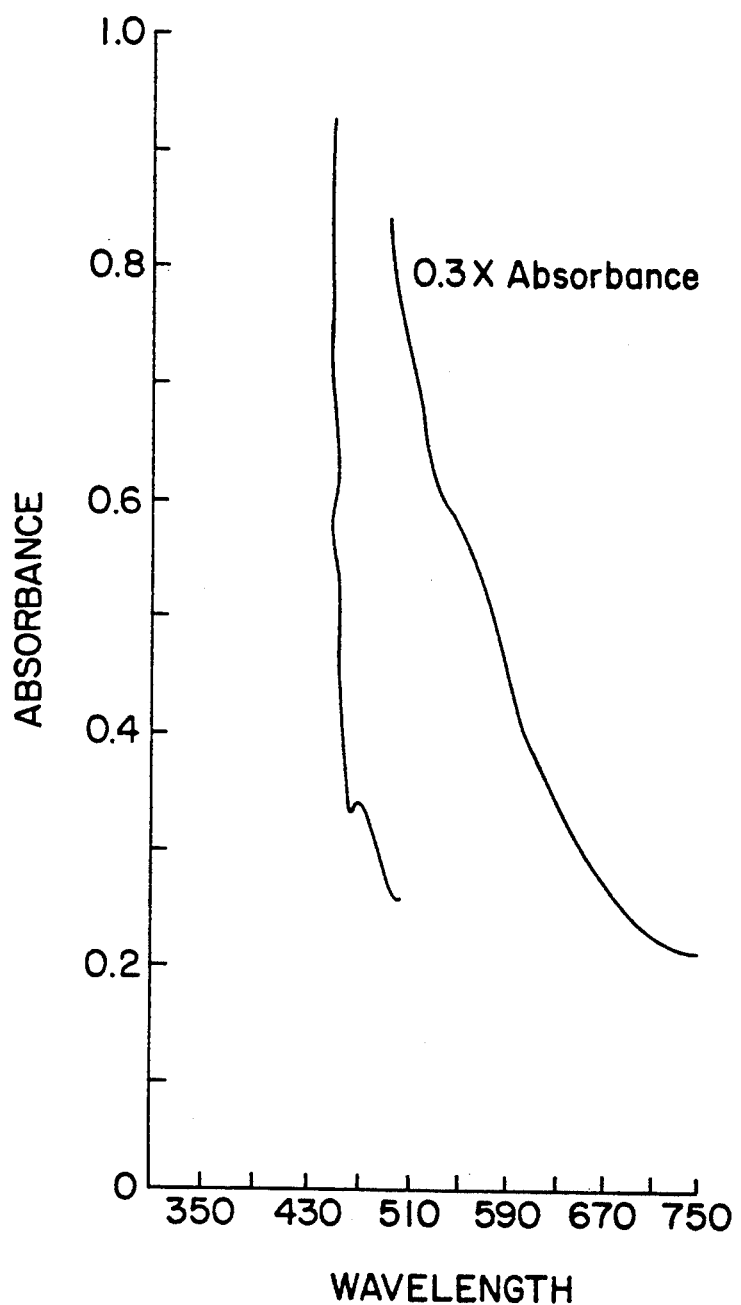
FIG. 2 is a UV/VIS spectrum recorded through a film at $C_{60}$ on a glass slip (designated Slip #2) having a vapor deposited fullerene surface (ca. 50nm thickness).
Figure 3:
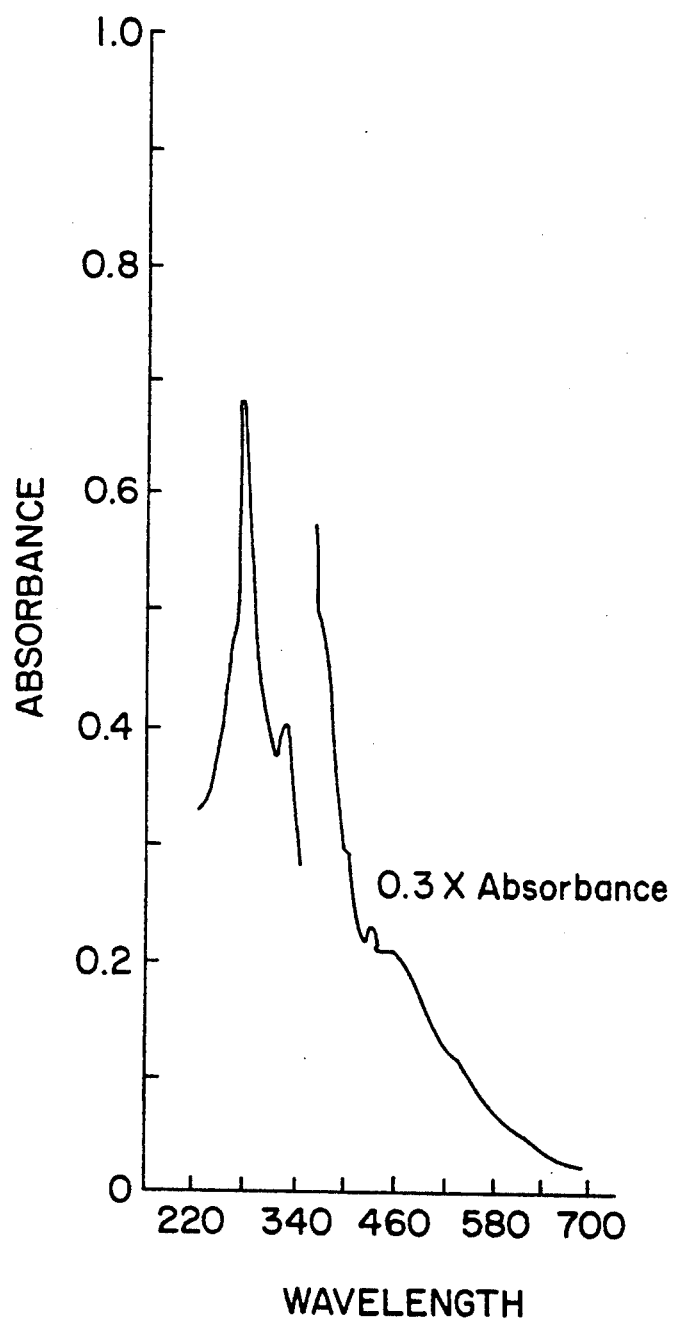
FIG. 3 is a UV/VIS spectrum of $C_{60}$ dissolved in 1 ml benzene from Slip #2.
Figure 4:
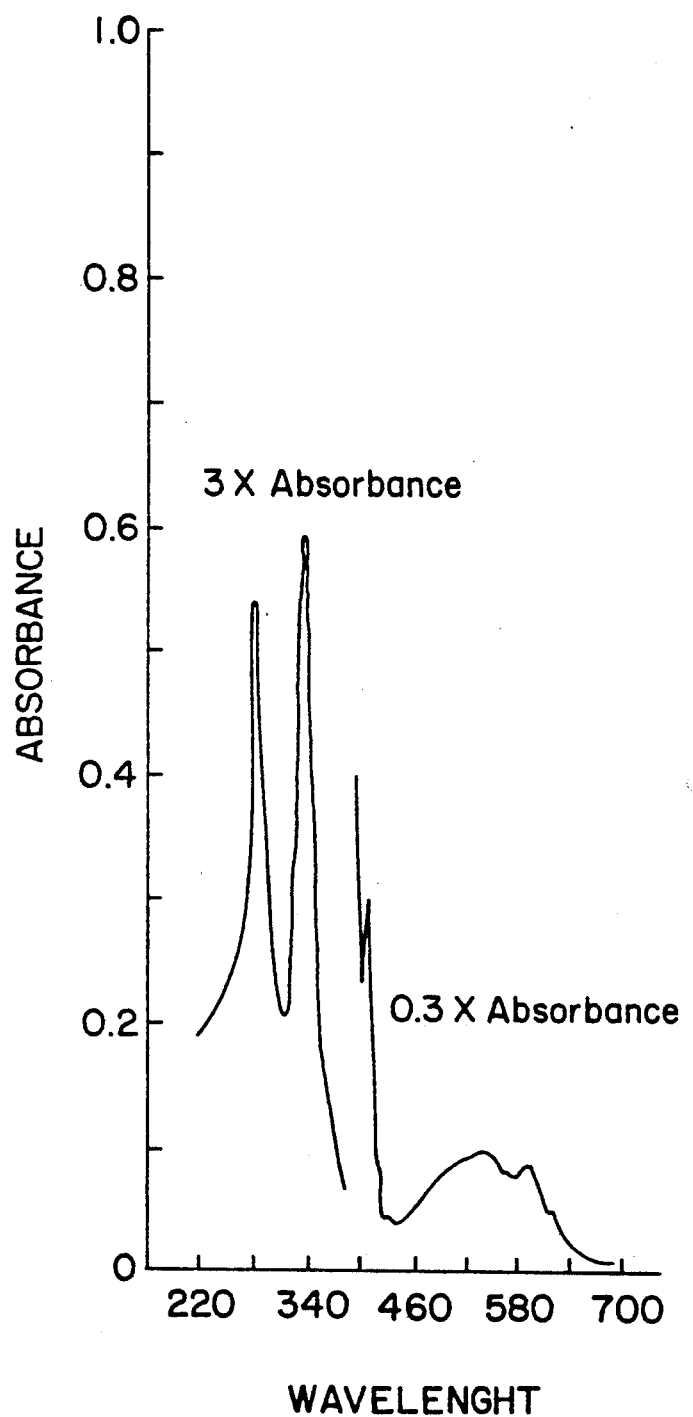
FIG. 4 is a UV/VIS spectrum of a 25 $\mu$mol/liter solution of authentic $C_{60}$ in benzene.

Both Slips #2 and #3 were regenerated by exposure to SPCA, followed by rinsing and air drying. Slip #2 was scanned directly in the spectrophotometer (FIG. 2; Ca 50nm thickness vapor deposited fullerene), and the fullerene was then dissolved in 1 ml of benzene and the spectrum of this solution was also determined (FIG. 3) and compared to that of authentic $C_{60}$ (FIG. 4; a 25 μmol/liter solution of $C_{60}$ in benzene). The thickness of the fullerene surface was too great to resolve spectral structure, but for a peak at 337 nm, corresponding to a peak reported for $C_{60}$ deposited on quartz (Kratschmer, W., et al., Nature 347:354–357 (1990)). The benzene solution was judged to contain a complex mixture of fullerenes, primarily of $C_{60}$, with the peak at 277 nm being specific for $C_{60}$. From the latter absorbance value, and using an extinction coefficient of $6.04 \times 10^4$ liter/mol.cm calculated from FIG. 4, the amount of $C_{60}$ contained on Slip #2 was estimated at about 8 μg.

Figure 5:
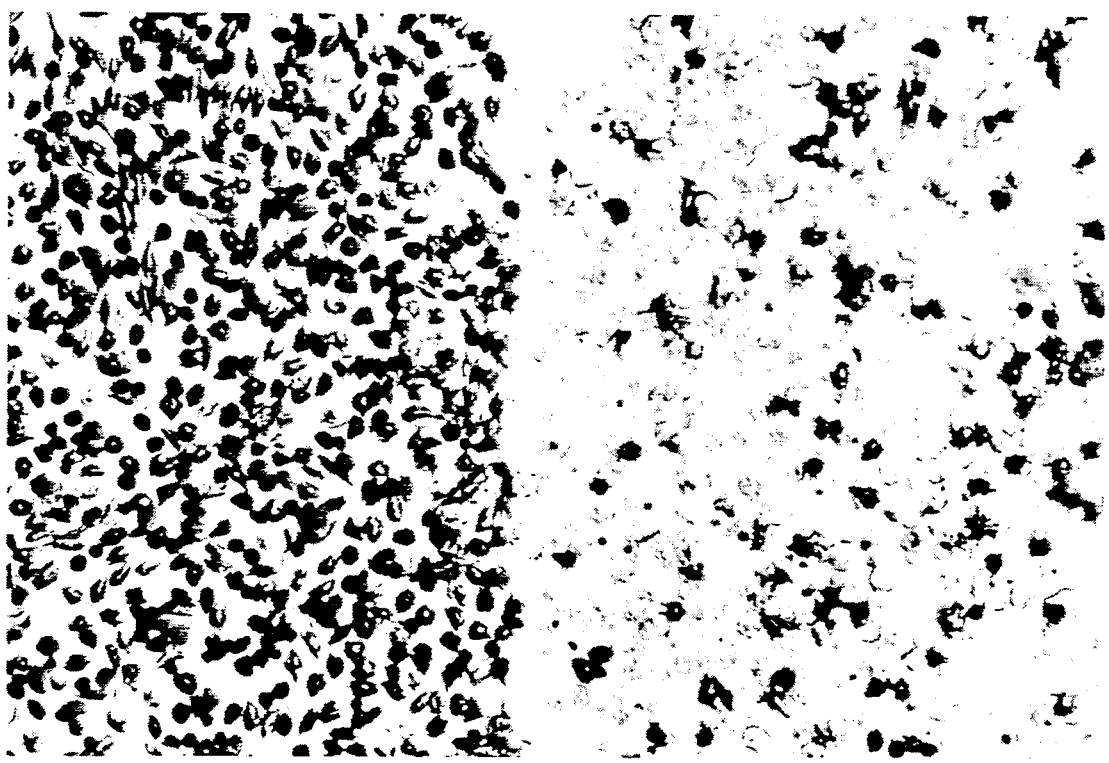
FIG. 5 shows CHO-AA8 cells grown to confluency on a SPCA-regenerated glass slip (Slip #3) and illuminated in the presence of oxygen followed by trypan blue staining, fixation and air drying (the left side of the field shows cells grown on the glass margin without fullerene coating; the right side of the field shows cells grown on the vapor deposited fullerene surface).

Slip #3 was regrown with CHO cells, and these were subjectively noted to grow more rapidly and with better spreading (i.e., attachment), on the surface than when the fullerene surface was directly used. When confluent with cells, the slip was equilibrated under 19% $O_2$ plus 5% $CO_2$ (balance $N_2$), illuminated for 30 minutes (177 J/cm$^2$), and then immediately exposed to trypan blue. Thereafter, cells were rinsed, fixed with buffered formaldehyde, rinsed again, and air dried. FIG. 5 shows the effect of illumination on the subsequent trypan blue uptake by these cells. Cells on the left half of FIG. 5 grew on the non-coated surface of the slip margin; cells on the right half grew on the deposited fullerene surface. Illumination in the presence of $O_2$ led to extensive membrane damage for cells only on the prepared surface such that a) substantial trypan blue uptake was observed (i.e., extensive membrane permeability), and b) cells on the prepared surface were "fried" in place (i.e., probably glued down by a reacted residuum) and did not pull up into refractile forms otherwise achieved during the drying process after fixation.

Figure 6:
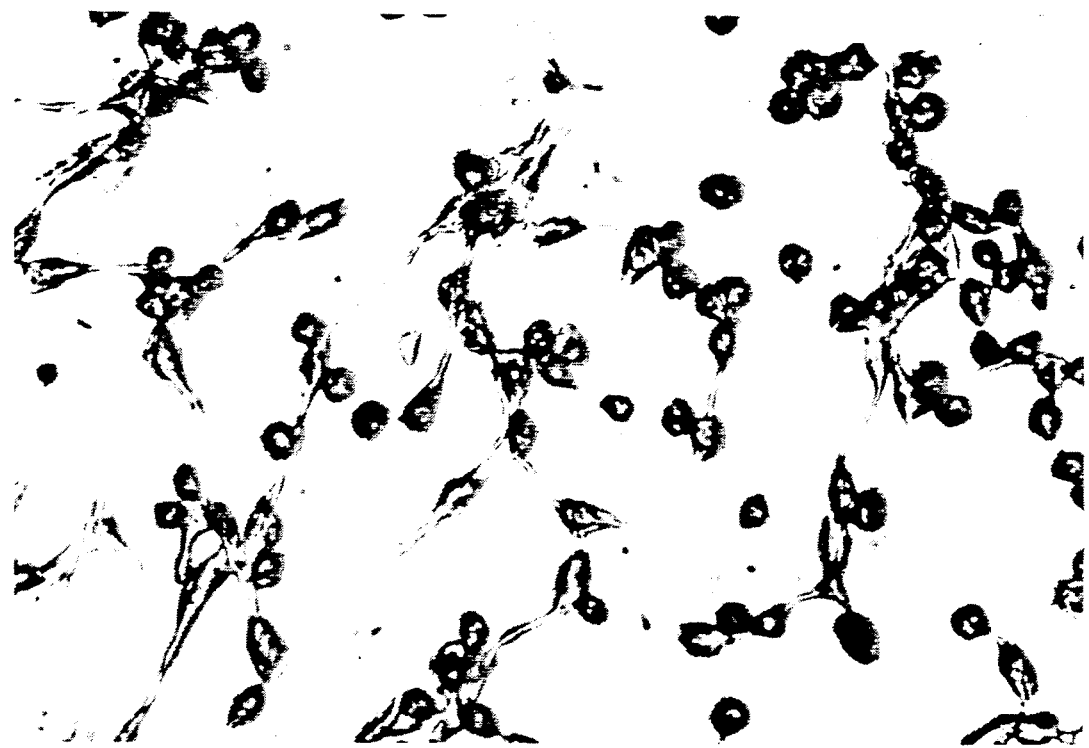
FIG. 6 shows CHO-AA8 cells grown to confluency on a SPCA-regenerated glass slide segment with a vapor deposited fullerene surface followed immediately (without illumination) by trypan blue staining, fixation, and air drying.
Figure 7:
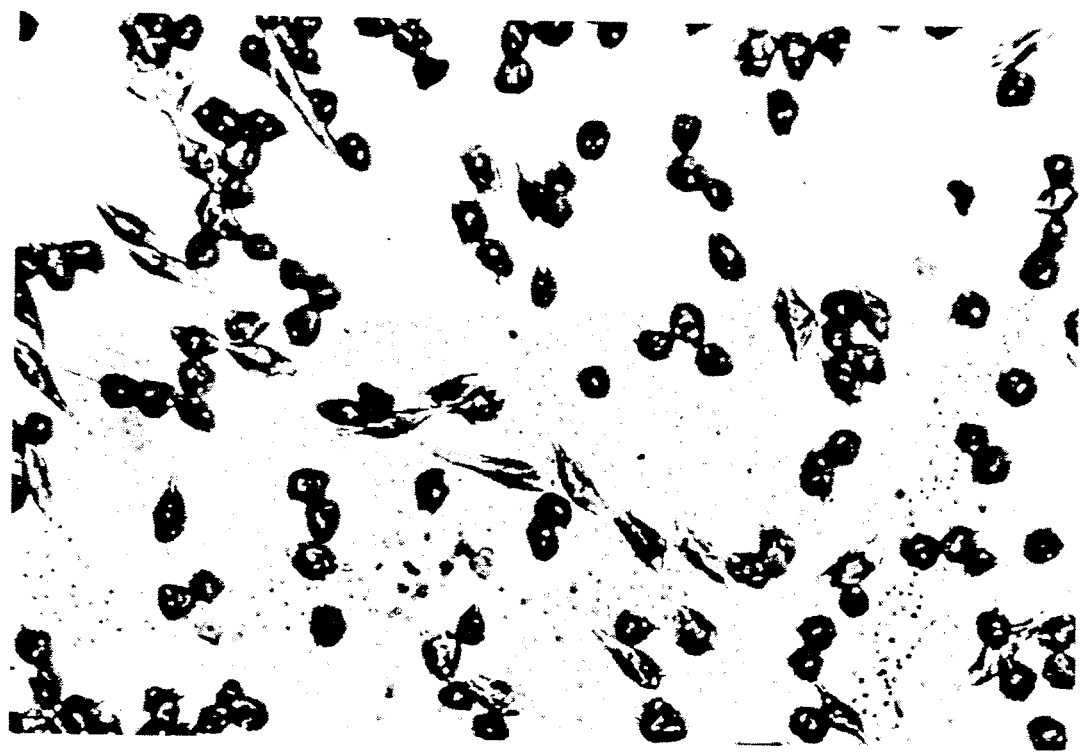
FIG. 7 shows CHO-AA8 cells grown to confluency directly on a SPCA-regenerated glass slip (Slip #3) and illuminated under 95% $N_2$ plus 5% $CO_2$ and followed immediately by trypan blue staining, fixation and air drying (the top half of the field shows cells grown on the glass margin without a fullerene coating; the lower half of the field shows cells grown on the vapor deposited fullerene surface).

The refractile cells on the non-prepared glass surface in FIG. 5 were not damaged as judged by lack of trypan blue uptake and by morphologic appearance that matched that of cells grown on a fullerene surface deposited on a glass slide segment without illumination (FIG. 6). Furthermore, the absolute dependence of $O_2$ on the light-induced damage to cells on the fullerene surface in FIG. 5 was established by regenerating Slip #3 with SPCA treatment, regrowing cells, equilibrating under 95% $N_2$ plus 5% $CO_2$, and illuminating for 30 minutes (177 $J/cm^2$) (FIG. 7). In this situation, trypan blue uptake was not observed and cells appeared as in FIG. 6 after fixation and air drying.

Figure 8:
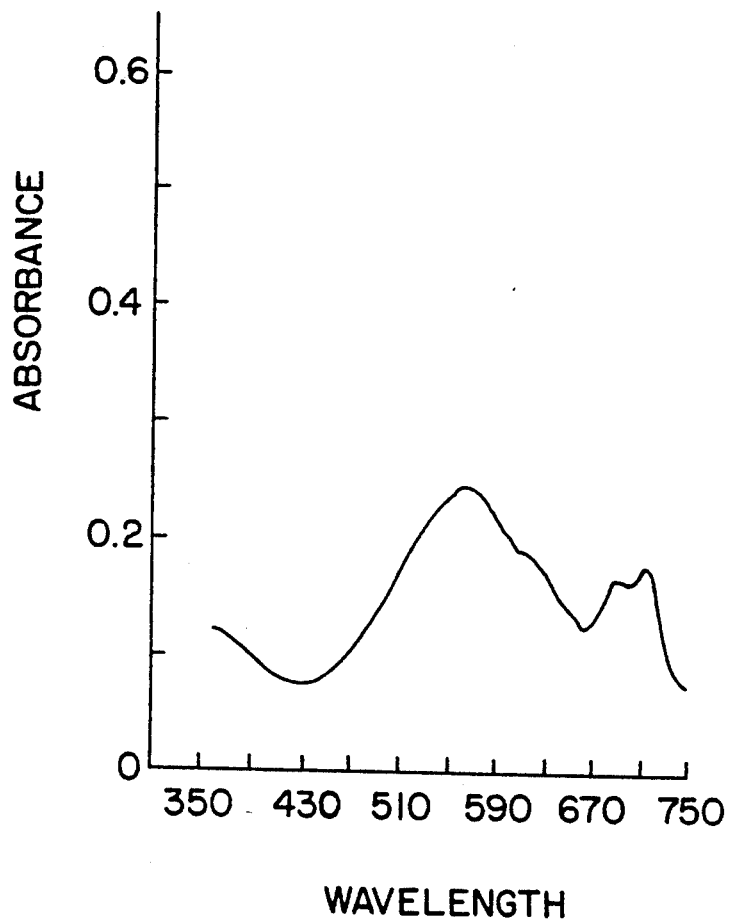
FIG. 8 is a UV/VIS spectrum of trypan blue recovered by a SPCA dissolution of CHO-AA8 cells grown to confluency on SPCA-regenerated glass slip (Slip #3) and illuminated in the presence of oxygen followed by treatment with trypan blue.
Figure 9:
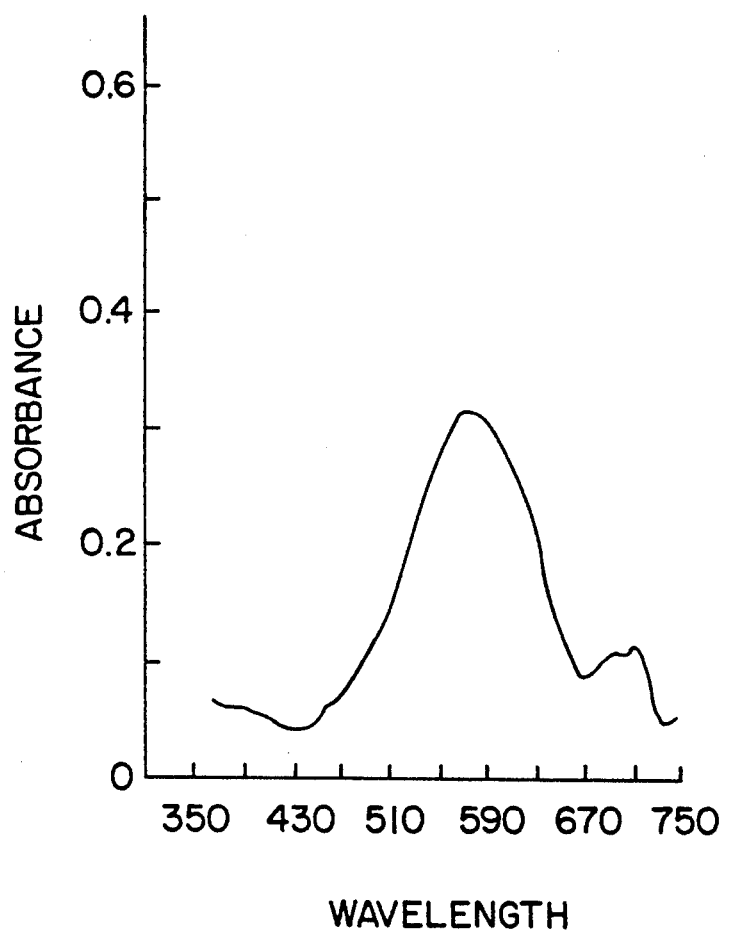
FIG. 9 is a UV/VIS spectrum of 4 mol/liter trypan blue in SPCA.

Trypan blue uptake by cells was quantitated with and without illumination. Slip #3 was regenerated again with SPCA treatment and cells were grown to confluency as usual. Illumination conditions that led to FIG. 5 were duplicated (19% $O_2$, 177 $J/cm^2$), followed then by the same exposure to trypan blue. After rinsing, cells were dissolved by SPCA, and the cell uptake of trypan blue was quantitated by spectrophotometry (spectrum shown in FIG. 8) to equal 1.1 Pg/cell using the extinction coefficient of $7.70 \times 10^4$ liter/mol.cm calculated at 582 nm for trypan blue dissolved in SPCA alone (spectrum shown in FIG. 9). Comparing FIGS. 8 and 9 it is noted that the major peak for trypan blue in the cell solution is blue-shifted by 14 nm. Slip #3 was again regenerated and cells again grown to confluency and identically treated except that light exposure was reduced by a third to 59 $J/cm^2$; trypan blue uptake was found to be 0.26 pg/cell, or about a four fold reduction, indicating an illumination dose response of cell membrane damage leading to trypan blue uptake. Recovery of trypan blue from nonilluminated confluent monolayers of cells growing on glass directly or on fullerene deposited on a slide segment was the equivalent of 0.08 pg/cell in both cases; this low level of trypan blue is probably recovered from the interstitial space of the cell monolayer.

Results above used fullerene surfaces on glass slips or slide segments that had not been scrupulously cleaned prior to fullerene vapor deposition. The resulting fullerene surface was uniform and durable with respect to fluid triturtations and autoclaving. An additional set of 17 glass slide segments was scrupulously cleaned by first rinsing in chloroform, polishing, and finally subjecting to ultrasonic cleaning in a methanol bath directly prior to fullerene vapor deposition. The integrity of the fullerene film was initially as good as that obtained on non-specially cleaned glass substrate. However, autoclaving produced multiple fractures of the surface that was also then susceptible to loss by gentle rinsing. In addition, gentle contact with fluids served to fracture and wash away substantial sections of the fullerene surface on non-autoclaved segments. Autoclaved slide segments were found to have reestablished a bonded fullerene surface. However, after three months of storage in the dark under ambient conditions, either slow complexation of fullerene to the cleaned glass substrate, or reemergence of containments or charged groups on the glass substrate originally removed by cleaning and important to fullerene complexation, or both, are hypothesized to explain the latter observation.

EXAMPLE 5: ASSESSMENT OF CELL MEMBRANE PERMEABILITY FOLLOWING ILLUMINATION OF CELLS ON A POLYSTRYENE SUBSTRATE PREPARED BY FULLERENE VAPOR DEPOSITION

Polystyrene dishes, termed petri dishes, are hydrophobic such that water droplets bead up on their surface. Petri dishes that are treated with negatively charged chemical groups in a commercial proprietary process are termed tissue ware dishes and are hydrophilic such that water droplets spread out in a film on their surface. Mammalian cells will attach to the surface of tissue ware dishes, but are generally said not to attach to the surface of petri dishes. Fullerene was deposited on both petri dishes and tissue ware dishes. Following this deposition, both dishes were observed to be equally hydrophobic as determined by water droplet beading that was equivalent to that seen with petri dishes directly. Interestingly, beading of water droplets on vapor deposited fullerene surfaces on glass slide segments was less pronounced than on directly deposited fullerene on polystyrene, although more pronounced than on directly deposited fullerene on glass. It is hypothesized that long range ionic forces in the glass substrate are preserved to some degree across the thin fullerene film. The fullerene surface on both petri and tissueware dishes was found to be very uniform and of good durability when rinsed with liquids.

CHO cells were seeded into both petri dishes and tissue ware dishes directly after fullerene deposition, and attachment and growth were observed under the microscope. Attachment was relatively poor. Over the course of 4 days at 37° C. it was clear that cells were actively dividing, but this growth was out into suspension, not on the fullerene surface where the number of cells attached in both rounded and flattened forms equalled about a third of what would be seen on glass or tissue ware surfaces, and the flattened, i.e., well attached cells, approximated only about 10-20% of the total. Pretreating the fullerene surface with SPCA for 2 hours at 33° C. prior to growing cells resulted in better cell attachment. Growing cells on the fullerene surface and then regenerating the dish for reuse by dissolving these cells with SPCA for 2 hours at 33° C. resulted in a more hydrophilic surface and improved cell attachment. Dishes identically regenerated with SPCA followed by treatment with poly-L-lysine (as is typically done with polystyrene in order to create a surface favorable for cell attachment) resulted in a more hydrophilic surface and improved cell attachment.

Although glass slips and slides are supplied as "precleaned" from the manufacturer, there is obviously some thin, unidentified deposit on the glass surface. Also, it is common practice not to clean "precleaned" microscope slides for mounting tissue sections for histological work-up because paraffin-blocked tissue sections do not stick as well to truly clean slides. It was similarly found in this work that fullerene vapor deposited films initially did not stick well to a scrupulously clean glass substrate, but that good bonding of these films did develop over three months of dark storage under ambient conditions. Fullerene films did stick rather well initially to non-cleaned clips and slide segments. Furthermore, fullerene films were found to stick relatively well to scrupulously clean polystyrene substrate. From these three latter observations it appears that fullerene vapor deposition requires contact with organic or other bonding molecules at the surface of a plastic or glass substrate to form bonds sufficient to withstand mechanical stress, such as encountered with autoclaving or triturating which are typical in tissue culture techniques.

Cells seeded on glass surfaces coated with fullerene grow and attach on the surface better (the latter was qualitatively judged by degree of rounding observed for cells attached to the surface) than cells seeded on polystyrene coated with fullerene. Regardless of whether fullerene was deposited on a modified polystyrene surface (i.e., hydrophilic surface), the fullerene coated surface was found to be hydrophobic as indicated by the beading of water in these dishes. In contrast, glass slips or slide segments coated with fullerene were notably less hydrophobic, though not as hydrophilic as the glass substrate itself. It is commonly acknowledged that a hydrophilic surface is necessary to achieve significant mammalian cell attachment. Thus, it appears that a glass substrate may establish hydrophilic centers across a thin (ca. 50 nm estimated maximum) fullerene surface, and that such hydrophilicity may be established by long range ionic perturbations caused by monovalent and divalent cations found in glass but not polystyrene. Thus, the readily manipulated hydrophobic and hydrophilic nature of the fullerene surface may allow selection of cell type in culture techniques, e.g., preferential attachment of polymorphonuclear leukocytes which are known to selectively adhere to plastic such as polyethylene or polypropylene.

Those skilled in the art will recognize, or be able to ascertain using no more than routine experimentation, numerous equivalents to the specific procedures described herein. Such equivalents are considered to be within the scope of the this invention and are covered by the following claims.

We claim:

1. A substrate comprising a fullerene-coated surface having a biological substance attached to the fullerene-coated surface.

2. A substrate of claim 1 wherein the fullerene comprises $C_{60}$, $C_{70}$, or a mixture of $C_{60}$ and $C_{70}$.

3. A substrate of claim 1 wherein the substance is selected from the group consisting of a cytokine, a lectin, a hormone, a growth factor, an oncogene product, a monoclonal antibody, an ion channel complex, an antigen receptor, DNA, RNA, polyethylene glycol, glycogen, a drug, an aromatic molecule, a steroid, a phospholipid, a long chain aliphatic substance and an attachment factor.

4. A cell culture substrate comprising a surface coated with fullerene sufficient to support the attachment and growth of cells.

5. A cell culture substrate of claim 4 wherein the fullerene comprises $C_{60}$, $C_{70}$ or a derivative of $C_{60}$ or $C_{70}$.

6. A cell culture substrate of claim 4 wherein the fullerene comprises a mixture of $C_{60}$ and $C_{70}$.

7. A cell culture substrate of claim 6 wherein the substrate comprises a ceramic, a polymer, or a carbon matrix.

8. A cell culture substrate of claim 7 wherein the ceramic is glass or quartz.

9. A cell culture substrate of claim 7 wherein the polymer is selected from the group consisting of polystyrene, polypropylene, polyhydroxyethyl methylacrylate, polyethylene terephthalate, polytetrafluoroethylene and nylon.

10. A cell culture substrate of claim 9 wherein the polymer is polystyrene.

11. A cell culture substrate of claim 7 wherein the substrate is selected from the group consisting of a cell-culture flask, a cell culture dish, cell culture microcarriers, cell culture macrocarriers, cell culture films and cell culture fibers.

12. A cell culture substrate of claim 4 wherein the fullerene is selected from the group consisting of $C_{60}$, $C_{70}$, $C_{76}$, $C_{78}$ and $C_{84}$ or mixtures thereof.

13. A cell culture substrate of claim 4 wherein the fullerene is coated on the surface of the substrate by a method selected from the group consisting of: sublimation of fullerene under vacuum; heating of purified fullerene; heating of unprocessed fullerene-containing soot; ion-sputtering of purified fullerene; ion-sputtering of unprocessed fullerene-containing soot; evaporative deposition of a solvent containing purified fullerene; and evaporative deposition of a solvent containing unprocessed fullerene-containing soot.

14. A cell culture substrate of claim 4 further comprising a substance attached to the fullerene-coated surface for interaction with cells attached to the fullerene-coated surface.

15. A cell culture substrate of claim 14 wherein the substance is selected from the group consisting of a cytokine, a lectin, a hormone, a growth factor, an oncogene product, a monoclonal antibody, an ion channel complex, an antigen receptor, DNA, RNA, polyethylene glycol, glycogen, a drug, an aromatic molecule, a steroid, a phospholipid, a long chain aliphatic substance and an attachment factor.

16. A cell culture substrate of claim 4 further comprising cells attached to the fullerene coated surface.

* * * * *